United States Patent [19]
Nehring

[11] 3,983,872
[45] Oct. 5, 1976

[54] SELF-CONTAINED FLUID EVACUATOR

[75] Inventor: John R. Nehring, Woodcliff Lake, N.J.

[73] Assignee: International Paper Company, New York, N.Y.

[22] Filed: Apr. 15, 1975

[21] Appl. No.: 568,205

Related U.S. Application Data

[63] Continuation-in-part of Ser. No. 417,124, Nov. 19, 1973, Pat. No. 3,889,677.

[30] Foreign Application Priority Data

| Nov. 18, 1974 | Australia | 75454/74 |
| Nov. 18, 1974 | Belgium | 150626 |
| Oct. 25, 1974 | Canada | 212332 |
| Nov. 18, 1974 | France | 74.37974 |
| Nov. 14, 1974 | United Kingdom | 49299/74 |
| Nov. 19, 1974 | Netherlands | 7415068 |

[52] U.S. Cl. ............................................. 128/278
[51] Int. Cl.² ........................................ A61M 1/00
[58] Field of Search ....................... 128/276–278, 128/274; 417/383, 389, 394; 222/386.5; 141/7, 65, 67; 138/30

[56] References Cited
UNITED STATES PATENTS

| 2,074,223 | 3/1937 | Horiuchi | 128/276 |
| 3,635,607 | 1/1972 | Grise | 417/394 |
| 3,875,941 | 4/1975 | Adair | 128/278 |

FOREIGN PATENTS OR APPLICATIONS

| 35,387 | 11/1965 | Germany | 128/274 |

*Primary Examiner*—Robert W. Michell
*Assistant Examiner*—Henry S. Layton
*Attorney, Agent, or Firm*—Finnegan, Henderson, Farabow & Garrett

[57] ABSTRACT

A wound evacuator is disclosed which is adapted for use with an external negative pressure source to provide continuous fluid evacuation and which includes its own negative pressure source to provide limited time duration evacuation. The evacuator includes a substantially rigid container and an air inflatable member within the container, the container and inflatable member having a combined configuration which avoids unnatural deformation of the inflatable member by the container in at least one direction of expansion of the inflatable member. Means are provided for inflating the inflatable member and controlling the deflation thereof and for controlling the sequence of sealing of the inlet and outlet ports by the inflatable member.

23 Claims, 17 Drawing Figures

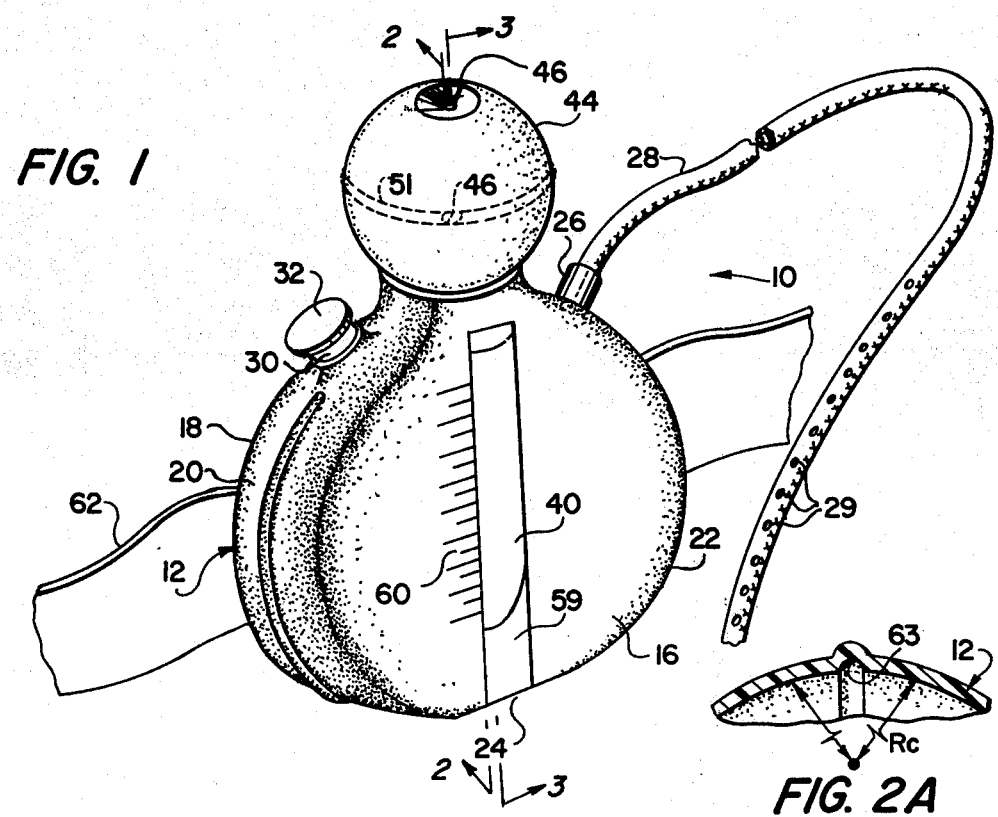
FIG. 1
FIG. 2A
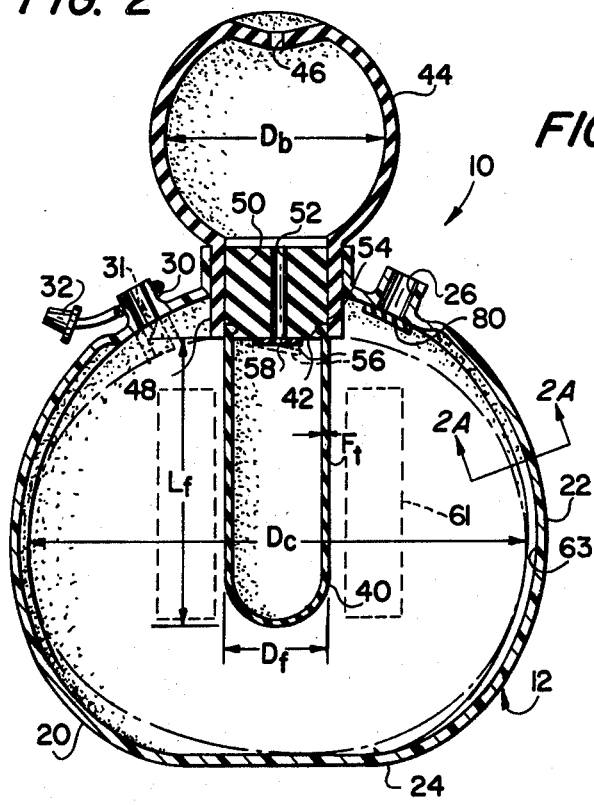
FIG. 2
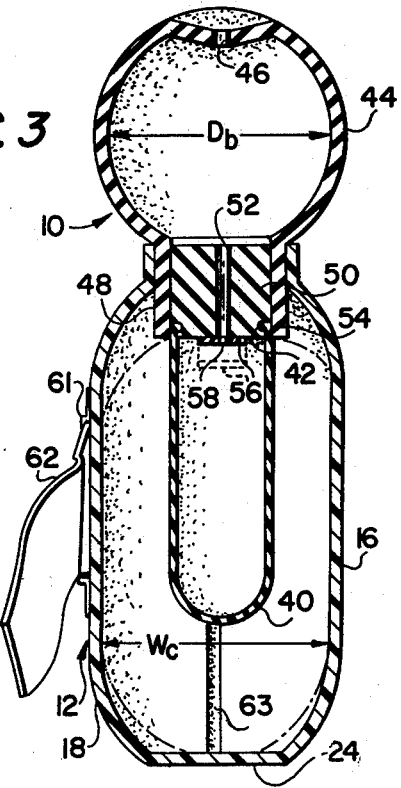
FIG. 3

SELF-CONTAINED FLUID EVACUATOR

BACKGROUND

This is a continuation-in-part of application Ser. No. 417,124, filed Nov. 19, 1973, now U.S. Pat. No. 3,889,677.

This invention relates to fluid evacuators and, more particularly, to such evacuators which are disposable, portable and substantially self-contained.

The evacuation of fluids from the body of a patient is a common medical practice. For example, the removal of fluids from the vicinity of a wound has been found to aid faster and firmer healing and reduce the likelihood of infection, fever and patient discomfort. Fluid evacuation usually is accomplished through gravity drainage, pressure dressings, compression bandages or by negative pressure, the latter being preferred. Conventional continuous closed wound suction devices include power driven vacuum pumps, central suction systems or evacuated bottles. With the exception of the evacuated bottle, each of these systems has many disadvantages because of their cost, noise and restriction of patient mobility resulting in the retardation of post operative exercises, ambulation and rehabilitation.

Other suction wound drainage systems were developed to overcome these disadvantages. Examples of more recent commonly used wound evacuators are shown in U.S. Pat. Nos. 3,115,138 and 3,376,868. In both of these devices the evacuator comprises an evacuation chamber formed with resilient side walls which, after manual compression and release, tend to return to their original extended position. In so returning they provide a reduced pressure on the interior of the container which, when attached to the patient by means of a tube, effects evacuation of the wound. A potential hazard with such a device is the possibility of accidental compression of the container at a time when compression is undesirable. Accidental compression when the device is attached to the patient could result in the injection of air or previously removed fluids into the patient. Another disadvantage with devices of this type is their wide variation of negative pressure over the specified filling range of the devices. When empty and fully compressed these devices often provide a vacuum higher than necessary which might cause lesions if tissue is sucked into or against the drainage tube. On the other hand, as the container becomes filled with fluid the vacuum is reduced often to a level where the vacuum is relatively ineffective and clots or other debris may clog the drainage tube. Wound evacuators presently commercially available have total pressure variations of about 130% or more.

Accordingly, it is an objective of this invention to provide an inexpensive, reliable, disposable, portable, self-contained vacuum drainage device which evacuates fluids from wounds at relatively constant pressure throughout the entire operating range of the device.

It is another objective of this invention to provide an improved self-contained wound evacuator which cannot be easily accidentally pressurized thereby avoiding accidental injection of air or fluids into a patient.

A still further objective of this invention is to provide an improved wound evacuator which is adapted for use with an external negative pressure source in order to provide continuous fluid flow evacuation and which also includes its own negative pressure source to form a totally self-contained unit.

Additional objectives and advantages of the invention will be set forth in part in the description which follows, and in part will be obvious from the description, or may be learned by practice of the invention. The objectives and advantages of the invention may be realized and attained by means of the instrumentalities and combinations particularly pointed out in the appended claims.

BRIEF DESCRIPTION OF THE INVENTION

To achieve the foregoing objectives and in accordance with the purpose of the invention, as embodied and broadly described herein, the self-contained fluid evacuator of this invention comprises a substantially rigid container having an inlet and an outlet passageway communicating with the interior thereof, an inflatable member within the container, inflating means for inflating the inflatable member, means for deflating the inflatable member, the inlet passageway being adapted to receive a conduit, the outlet passageway being adapted to be connected in fluid flow communication with a negative pressure source. Means are provided for ensuring that one of the inlet and outlet passageways does not become abturated by the inflatable member before the other of the inlet and outlet passageways.

Preferably, the evacuator includes flow control means for enabling fluid to enter the inflatable member at a higher rate than the fluid can leave the inflatable member.

In accordance with the other embodiments of this invention, a fluid evacuator adapted for use with an external vacuum source, comprises a substantially rigid, closed container including a bottom wall, first and second spaced apart opposed side walls, third and fourth side walls joined to the opposite ends of the first and second side walls, the third and fourth side walls being spaced apart a distance greater than the spacing between the first and second side walls. The evacuator further includes inlet and outlet passageways communicating with the interior of the container, an inflatable member within the container, means for inflating the inflatable member, means for deflating the inflatable member, means for controlling the sequence in which the inflatable member can obturate the inlet and outlet passageways, and wherein the third and fourth side walls have a configuration which substantially conforms to the shape of the natural unimpeded shape of the adjacent portion of the inflatable member during inflation of the inflatable member effecting substantially constant negative pressure at the port during inflation of the inflatable member.

Preferably the configuration of the third and fourth side walls either actually conform to the shape of the adjacent portion of the inflatable member or effectively conform to that shape through control of the pressure within the container.

The invention consists in the novel parts, constructions, arrangements, combinations and improvements shown and described. The accompanying drawings, which are incorporated in and constitute a part of the specification, illustrate several embodiments of the invention and, together with the description, serve to explain the principles of the invention.

BRIEF DESCRIPTION OF THE DRAWINGS

Of the drawings:

FIG. 1 is a perspective view of a wound evacuator formed in accordance with this invention;

FIG. 2 is a sectional view taken along line 2—2 of FIG. 1;

FIG. 2A is a sectional view taken along line 2A—2A of FIG. 2;

FIG. 3 is a sectional view taken along line 3—3 of FIG. 1;

DETAILED DESCRIPTION OF A PREFERRED EMBODIMENT

Figure 4:
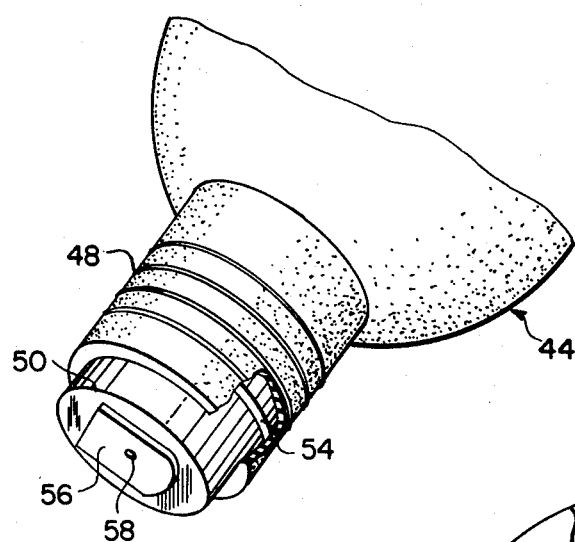
FIG. 4 is an enlarged, partially cutaway, perspective view of the throat portion of a pressurized air source formed in accordance with one form of this invention.

Throughout the specification and claims, terms of orientation, such as front, back, up and down are employed with respect to the orientation shown in the drawings in order to simplify description of the invention and are not intended to limit the location or direction of the elements with respect to which these terms are used.

In accordance with the invention, the wound evacuator includes a housing and a first port serving as a fluid inlet port communicating with the interior of the housing. The first port is adapted to receive a tube designed to be placed internally within a patient adjacent to a wound in order to remove fluids from the vicinity of the wound. As here embodied, a self-contained wound evacuator 10 is formed with a container 12 having opposed first and second side walls 16, 18 (hereinafter called front and back walls), opposed third and fourth side walls 20, 22 adjacent to the front and back walls 16, 18 and a bottom wall 24. The container 12 is relatively rigid, which means that it will not deform substantially when it is subjected to the normal forces to which devices of this sort are expected to be exposed. The container 12 is provided with at least one port, such as port 26, extending through and communicating with the interior of the container 12. The port 26 is adapted to receive flexible tubing 28 which is to be inserted into a patient adjacent to the wound being treated. The tubing 28 is conventional wound tubing which is non-toxic, non-pyrogenic, inert, non-porous and non-degradable when used in its intended environment and which has a plurality of openings 29 at its distal end.

While a single port 26 is sufficient for operation of the self-contained wound evacuator 10 as described below, it is preferred that a second port 30 be provided to serve as an outlet port to permit expulsion of air contained within the container 12 and to permit removal of fluid which is received within the container 12 during utilization of the wound evacuator 10. A suitable closure or cap 32 is provided to permit selective opening and closing of the second port 30.

In accordance with the invention an air inflatable member is mounted within the container 12 and means for inflating and deflating the inflatable member are provided. As here embodied, the inflatable member is a resilient bladder 40 having an opening at one end 42 thereof. A means for inflating the bladder 40 preferably is a manually operated pump, such as a hand-operated bulbous resilient member having a resiliency at least only slightly greater than the resiliency of the bladder 40. Such a resilient member is a rubber bulb 44 having an air inlet 46 and an open neck 48. The open end 42 of the bladder 40 is mounted in the neck 48 of the bulb 44 so that air expelled through the bulb neck 48 is forced to enter the bladder 40. While the bladder can be mounted directly on the walls of the bulb neck 48, the embodiment illustrated in FIG. 2–4 employs a plug 50 which is force-fitted within the neck 48, the plug 50 having an air passageway 52 axially therethrough. The plug 50 is provided with an annular recess 54 to receive the open end 42 of the bladder, the open end of the bladder being trapped between the exterior of the plug 50 and the interior of the blub neck 48 to fixedly hold the bladder in place. The bulb 44 serves as the means to inflate the bladder 40 while the resiliency of the bladder serves as the means for deflating the bladder.

While the bulb air inlet 46 is shown at the top of the bulb 44, it could be located at any other position. For example, with a container 12 as shown, locating the air inlet on the side has been found particularly convenient because it is easier to block the air inlet 46 with a finger or the heel of a hand. Furthermore, in order to ensure quick opening of the inlet 46 on release of the bulb so that the bulb quickly refills with air entering through the inlet 46 rather than being withdrawn from the bladder 40, an irregular surface, such as a bead 51 is provided through which the inlet is formed. The bead 51 prevents the finger or hand from sealing the inlet during return of the bulb to its normal unsqueezed condition.

Further in accordance with the invention, valve means are provided which are responsive to the difference in pressure between the bulb 44 and the bladder 40 so that when the pressure in the bulb exceeds the pressure in the bladder, the valve means permit free flow of air from the bulb to the bladder. However, when the pressure in the bladder 40 exceeds the pressure in the bulb 44, the valve means restrict the flow rate from the bladder to a predetermined minimal quantity.

In order to control the rate of deflation of the bladder 40, a slow leak check valve, such as a flapper valve 56 having a small diameter bleed vent 58 therethrough, is mounted on the bladder side of the plug 50. When the bulb 44 is squeezed, the flapper valve 56 permits air to be expelled freely from the bulb into the bladder 40 since the pressure differential across the flapper valve 56 during such an operation forces the flapper valve away from the plug 50 thereby permitting air to flow easily into the bladder 40. However, when the bladder is partially inflated and the bulb 44 is returning from its squeezed or collapsed position to its normal or expanded position, the pressure within the bladder is higher than the pressure within the bulb and the flapper valve is forced against the plug 50 thereby obturating the air passageway 52 except for the vent 58 and preventing most of the air from leaving the bladder 40. After the bladder is fully inflated and the wound tubing 28 is inserted in a patient for evacuation, the small bleed vent 58 permits air to be expelled from the bladder 40 through the passageway 52.

To utilize the self-contained wound evacuator 10 of this invention the distal end of the wound tubing 28 is inserted in the patient before the proximal end is connected to the inlet port 26. Alternatively, the wound tubing can be connected to the container 12 and closed by a conventional pinch clamp (not shown). The closure 32 is removed from the outlet port 30 and the bladder 40 is inflated by alternately squeezing and releasing the bulb 44. When squeezing the bulb 44 the user covers the air inlet 46 to prevent air from being expelled through the inlet, thereby requiring that all air expelled from the bulb 44 passes through the air passageway 52 into the bladder 40. When the bulb is released air enters the bulb through the inlet 46. The flapper valve 56 prevents a substantial amount of air from flowing from the bladder 40 back into the bulb 44. Continued pumping of the bulb inflates the bladder 40 which forces the air within the container 12 out through the outlet port 30 until such time as the inflated bladder substantially fills the container 22. At that time, the proximal end of the wound tubing 28 is connected to the inlet port 26 (or the pinch clamp is opened) and the closure 32 is placed in the outlet port 30 thereby closing the port. As the bladder deflates, the air in the bladder passes outwardly through the bleed vent 58, the air passageway 52 and the bulb air inlet 46. Deflation of the bladder 40 produces a negative pressure at the port 26 which causes fluids in the vicinity of the openings 29 at the distal end of the wound tubing 28 to pass through the tubing into the container 12.

After the container 12 is filled with body fluid, the closure 32 is removed from the port 30 and the container is emptied, either by gravity feed (pouring the fluid out through the port) or by attaching the port 30 to the low pressure side of a pump and pumping the fluid out. The body fluid can also be expressed from the container 12 by closing the pinch clamp and pumping the bulb 44. As the bladder inflates, it forces the body fluid out of the container and, when empty the bladder is fully inflated and the wound evacuator 10 is ready for reuse. If only a single port 26 is used, the container is drained through the port 26.

In order to provide substantially constant negative pressure at the inlet port 26 throughout the entire operating range of the wound evacuator 10, and to utilize substantially the entire volume of the container, the container 12 and the bladder 40 should have a combined actual or effective configuration so that the container does not physically interfere with or distort the inflation of the bladder 40 in at least one direction of inflation. The terms "constant pressure" and "substantially constant pressure" as used throughout this specification and in the claims are intended for use in a relative sense and do not imply absolute constant or unchanging pressure. For example a total pressure variation of up to about 20% – 30% throughout about 90% of the deflation range is acceptable.

A low profile container 12 (relatively narrow from front 16 to back 18) is preferred because it can be more comfortably and conveniently worn by a patient or attached to a support, such as a bed or chair. These advantages can be obtained if the front and back walls 16, 18 are substantially flat and relatively closely spaced apart. Substantially flat front and back walls are walls which either are truly flat or which have a radius of curvature much greater than the radius of the bladder 40 when the bladder contacts the front and back walls 16, 18. Where a substantial vacuum is to be induced in the container 12, it may be preferred to form the front and back walls 16, 18 with a shallow outward curvature (large radius of curvature) to provide structural strength without adversely affecting the low profile of the container.

It also is desirable to be able to stand the container 12 vertically on a flat surface and, therefore, the bottom wall 24 of the container preferably should be flat.

It has been found that satisfactorily constant pressure can be obtained with a cylindrical bladder when the bladder is inflated in a low profile container ("flat" front and back walls) if the side walls 20, 22 adjacent to the flat front and back walls 16, 18 actually or effectively conform to the shape of the inflated bladder 40.

In order to actually conform the side walls 20, 22 to the bladder shape, the side walls 20, 22, are formed with a transverse outward curvature (from front wall to back wall) as can be seen in FIG. 2A. Preferably, the radius of transverse curvature is $W_c/2$ where $W_c$ is the distance between the front and back walls 16, 18. It also is desirable to avoid corners at the top and bottom of the side walls and, therefore, rounded upper and lower ends are formed or, alternatively, the side walls 20, 22 can be formed with a longitudinal curvature from top to bottom as can be seen in FIGS. 1 and 2.

While satisfactory results can be obtained over a relatively wide range of front-to-back wall spacing, more consistently reliable results and more useful filling volume for a given container size while maintaining relatively constant pressure can be obtained if the front and back walls 16, 18 are spaced apart a distance greater than twice the diameter of the uninflated bladder ($W_c > 2D_f$).

In accordance with this invention, instead of actually conforming the sidewalls 20, 22 to the inflated bladder shape, the side walls 20, 22 can be made to "effectively" conform to the bladder shape by controlling the pressure within the container. More specifically, with inlet port 26 closed as the bladder 40 is inflated, the air inside the container 12 is expelled through the outlet port 30 until after the bladder contacts the side walls 20, 22 and continues to inflate, it reaches a position within the container wherein the bladder is about to be forced into a shape which is different from what it would be if the side walls 20, 22 were nonexistent. At that time, the outlet port is occluded by the bladder to prevent further explusion of air from the container 12. Any further pressurization of the bladder 40 by pumping the bulb 44 results in a concommitant increase in pressure inside the container since the air cannot escape. Upon release of the bulb 40 the pressure in the bladder and container drops to atmospheric pressure by virtue of the air in the bladder 40 escaping through the check valve bleed port 58 and bulb air inlet 46 at a predetermined rate to the atmosphere. This concept of pressure equalization in the container and bladder when the bladder is about to be deformed into a shape which adversely affects a constant pressure curve is referred to throughout the specification and claims as effective conformation of the container shape with the bladder shape.

As here embodied, the outlet port 30 is occluded by the bladder 40 when it reaches its predetermined shape. This is effected by forming the outlet port 30 with an inwardly extending protuberance 31 which projects inwardly an amount calculated to bring in contact with the bladder at the appropriate bladder inflation level. The outlet port 30 and protuberance 31 can be formed as an integral part of the container 12 or it can be formed by a separate member mounted in an opening formed in the container 12. When this outlet port occluding concept is employed the shape of the container 12 is not critical.

With respect to a container which actually conforms to the bladder shape and which has a satisfactory low profile, substantially constant negative pressure during deflation of a bladder has been obtained with a container and latex cylindrical bladder having the shapes generally shown in FIGS. 2, 2A and 3 and having the following dimension ratios.

$D_f$ = diameter of bladder;
$L_f$ = length of bladder = 3.0 - 4.0 $D_f$
$W_c$ = width of container = 2.5 $D_f$
$R_c$ = radius of transverse curvature of side walls = $W_c/2$
$D_c$ = length of container = 1.8$L_f$
$P_c$ = container interior perimeter <22$D_f$ The bladder thickness ($F_t$) together with the characteristics of the bladder material (actually, the modulus of elasticity) determines the vacuum level produced within the container. For a latex bladder, a bladder thickness of 0.01 $D_f$ has been found to produce a constant negative pressure in the above described container of approximately 30 inches of water (see FIG. 5). The container perimeter/bladder diameter ratio is calculated to provide not greater than a seven fold increase in bladder perimeter which has been found to be within a safe stress range for a latex bladder. For a convenient and comfortable evacuator profile, the bulb diameter ($D_b$) should be approximately equal to the width of the container ($D_b = W_c$).

Figure 5:
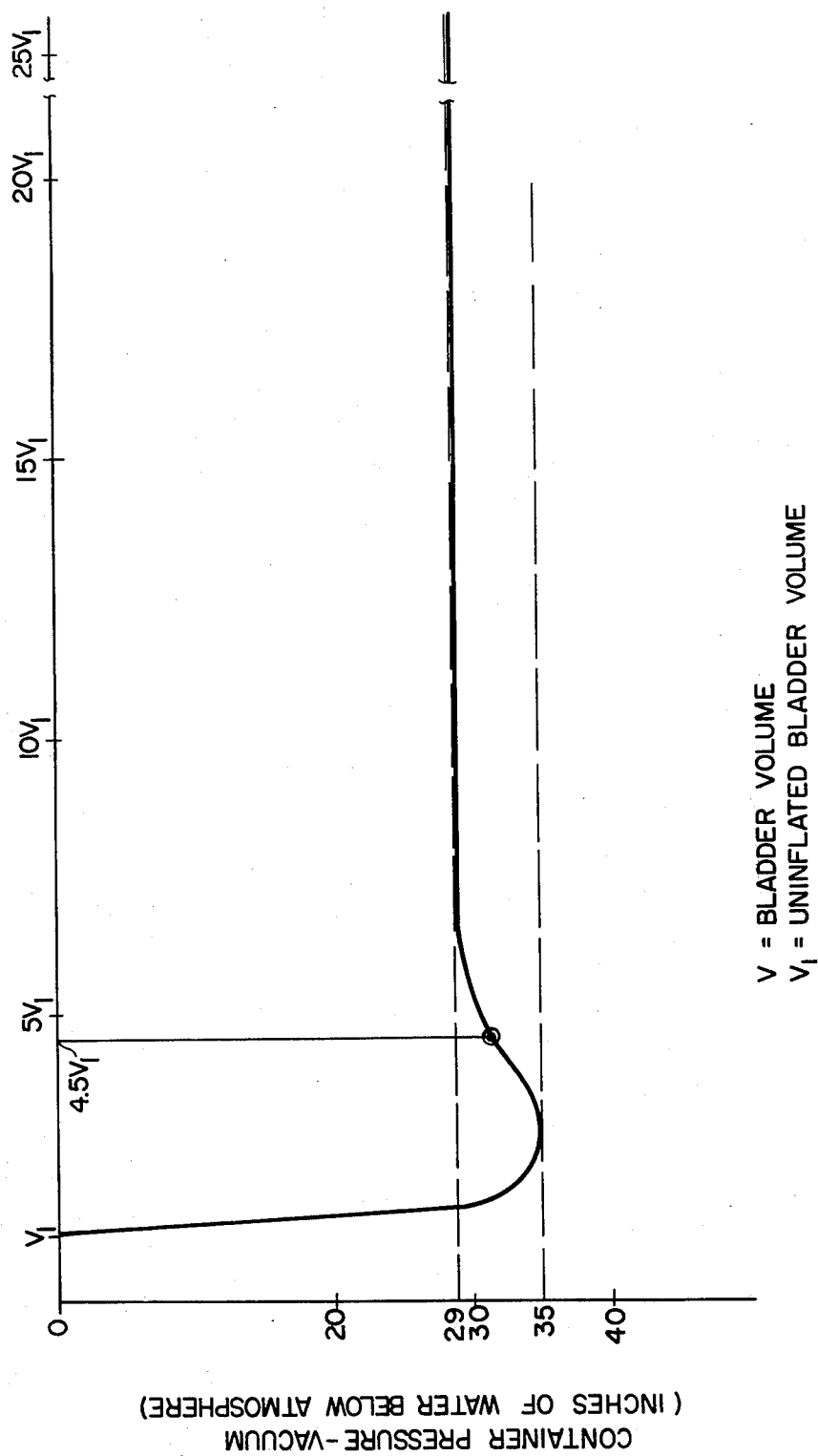
FIG. 5 is an empirical pressure vs. volume curve of a cylindrical latex bladder within a rigid container formed in accordance with this invention.

These ratios provide a self-contained wound evacuator having satisfactory performance by providing relatively constant pressure in a desired pressure range (−29 to −35 inches of water) and a safe stress for a bladder made of natural latex. The bladder can also be formed from any synthetic elastometer, such as polyurethane. FIG. 5 is a pressure vs. volume curve of a latex bladder having a ¾ inch uninflated diameter, a 2½ inches free length and a 0.012 inch wall thickness which was inflated in a rigid container having dimensions substantially in accordance with the above dimension ratios. As can be seen, the vacuum within the container remains between 31.3 inches of water at a bladder volume of about 4.5 times the uninflated bladder volume (4.5$V_1$) at which time the bladder first touched the relatively close container walls (e.g. 16, 18) and 29 inches of water. The pressure remains at this level throughout the operating range of the wound evacuator and satisfactory results have been obtained at bladder inflations of over 30$V_1$. The total pressure variation over this range was only about 8% of the minimum pressure within the range (29 inches of water). In connection with wound evacuators, the pressure curve of FIG. 5 is considered to have a substantially constant pressure.

The container 12 can be formed of any suitable material such as a moldable plastic, for example, polyvinyl chloride. The shape of the container lends itself to being blow molded; however, it could be formed other ways, such as by injection molding. At least a portion 59 of one of the flat side walls 16, 18 preferably is transparent and a calibrated graduated scale 60 is placed along the side thereof in order to enable volumetric measurement of the amount of fluid contained within the evacuator 10. The container 12 also can be provided with mounting tabs 61 to which a belt 61 or other support means is attached to facilitate hanging the wound evacuator 10 on a bed or chair or to enable the evacuator to be worn by an ambulatory patient.

Figure 6:
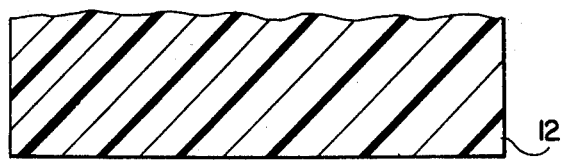
FIG. 6 is an enlarged sectional view of a portion of the wall of the wound evacuator container having a roughened interior surface.

Further in accordance with the invention, it is desirable to provide means for preventing accidental sealing off of a portion of the container from the outlet port 30, especially during evacuation of fluids from the container 12 which were removed from the patient. One means for avoiding this blockage is to provide a recess 63 in the interior surface of the container walls, particularly in the area leading to and adjacent to the outlet port 30. Such a recess 63 assures the existence of a fluid flow passageway from the interior of the container 12 to the outlet port 30. Also, the interior surface of the container walls can be roughened, such as by injection molding the container, to accomplish the same results (FIG. 6).

Figure 7:
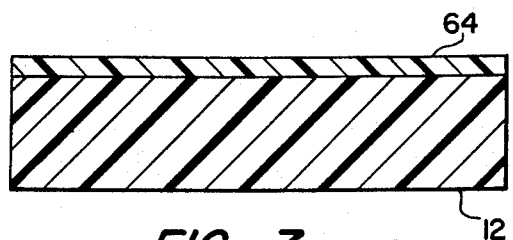
FIG. 7 is an enlarged sectional view of a portion of the wall of the wound evacuator container having a coating on the interior surface thereof.

A means for minimizing bladder 40 stress is to provide a surface coating 64 on the interior surface of the container 12, (FIG. 7) or on the exterior surface of the bladder 40, which will lessen adherence of the bladder to the interior of the container. For example, it has been found that chlorinating the surface of a latex bladder or coating the interior surface of a container with a conventional commercially available medical silicone fluid successfully lessens adherence of the bladder to the container walls, Reduction of the adherence of the bladder 40 to the container walls also is of substantial assistance in maintaining the negative pressure substantially constant.

In order to operate the resilient bulb 44 illustrated in FIGS. 2 and 3, it is necessary for the user to place his finger over the air inlet 46 while squeezing the bulb 44 to prevent air from escaping through the air inlet 46 and thereby forcing that air into the inflatable bladder 40. The combined operation of simultaneously closing the air inlet 46 and squeezing the bulb 44 is a safety feature to prevent accidental injection of air or previously removed fluid into the patient since it is unlikely that both steps will accidentally be performed. Furthermore, the relative rigidity of the container 12 also precludes accidental pressurization of the contents of the container 12 by pressing on the sides of the container. Consequently the structure provided by this invention reasonably assures that fluid or air will not be accidentally injected into the patient by accidental pressuring of the container.

Figure 8:
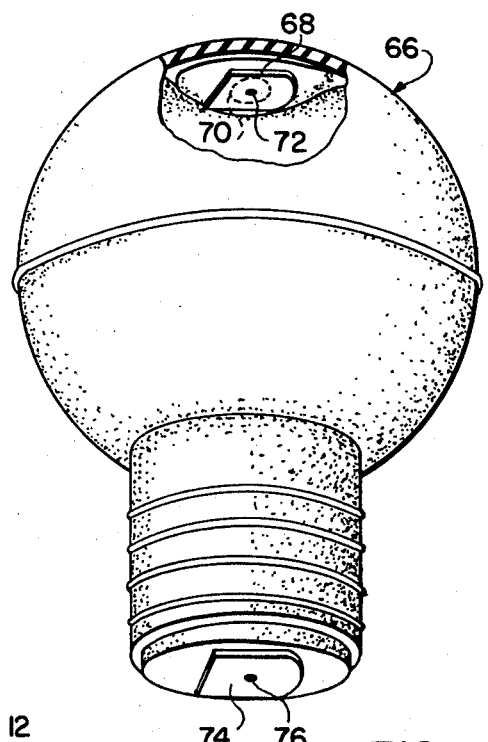
FIG. 8 is an enlarged, partially cutaway, perspective view of a pressurized air source formed in accordance with a second form of this invention.

With some sacrifice in safety but to simplify the utilization of the wound evacuator 10, another form of resilient bulb such as bulb 66, illustrated in FIG. 8, may be used which eliminates the need for the operator to cover the air inlet in order to effectively inflate the bladder 40. An automatically operating check valve, such as a flapper valve 68, is located on the interior surface of the bulb 66 to normally cover the air inlet 70 and is provided with a small diameter bleed vent 72. In order to inflate the bladder 40 the user squeezes the bulb 66 thereby increasing the pressure within the bulb. This increased pressure forces the flapper valve 68 against the air inlet 70 restricting the amount of air passing through the air inlet to be that small amount which can pass through the bleed vent 72. The pressure differential across the flapper valve 74 between the bulb 66 and the bladder 40 causes the flapper valve 74 to open and permit the air to freely enter the bladder 40. Upon release of the bulb 66, the resiliency of the bulb returns it to its original position increasing the volume within the bulb resulting in a reduced pressure within the bulb. This produces a pressure differential across the flapper valve 68 causing the flapper valve to open and allowing atmospheric air to enter the bulb through the inlet 70 while closing the flapper valve 74 to prevent escape of air from the bladder. After the bladder 40 is inflated sufficiently, and the bulb returns to its normal position, air leaving the bladder 40 flows through the bleed vent 76 in the flapper valve 74, into the bulb 66 and through the bleed vent 72 in the flapper valve 68 and to the atmosphere.

To further protect against accidental ejection of air or liquid through the port 26, a check valve, such as a flapper valve 80, can be mounted adjacent to the port 26 for closing the port 26 upon pressurization of the container, such as if the bulb 44 (or bulb 66) is accidently squeezed. Of course, the check valve 80 does not interfere with the flow of fluid into the container 12 through the wound tubing 28. Furthermore, the port 26 can be formed such that the bladder 40 occludes the port 26 when the bladder is inflated to its intended volume to further ensure against leakage through the port 26 to the patient.

It is also contemplated that a bulb can be used which has the same capacity as a fully inflated bladder. In other words, a single compression of the bulb would be sufficient to complete the inflation of the bladder. With a bulb of this size there is no requirement for an air inlet 46 and a closed system can be formed wherein air from the bulb fills the bladder and, when the bladder deflates, the air returns to the bulb for subsequent use. In such a closed system, a supple bulb, less resilient than the bladder, is used.

Further in accordance with this invention, the wound evacuator is adapted for use with an external negative pressure source, such as a conventional vacuum pump, in order to continuously evacuate fluid from the patient. This permits a surgeon to have the wound evacuator continuously fully operative while he performs surgery and closes up the wound site. During this period, there is no need to have a fully self-contained portable wound evacuator and reliance upon a vacuum pump to provide the negative pressure is not an inconvenience since the patient is immobile on the operating table. However, upon completion of the operation, the wound evacuator may be disconnected from the external vacuum source and become a self-contained wound evacuator.

For a wound evacuator which is adapted to be attached to an external vacuum source the inlet and outlet ports should be designed so that the inlet port does not become closed or sealed by the bladder prior to sealing of the outlet port. Otherwise, the external vacuum source could be operating without effecting removal of fluid from the patient. When the wound evacuator container is properly shaped to actually conform to the bladder shape and provide substantially constant negative pressure during deflation of the bladder as is described above, it is preferred that the inlet and outlet ports not be sealable from each other, or in other words that neither of the inlet or outlet ports be sealed prior to the other, in order to ensure continuous fluid flow between the inlet and outlet. When the container is other than ideally shaped, such as is described above with respect to forming the container to effectively conform to the bladder shape by controlling the pressure within the container, it may be desirable to have one of the ports sealable by the bladder either separately or simultaneously with the other port. For example, by suitable positioning of the outlet port, the bladder could be inflated and seal the outlet port prior to the bladder being distorted from its free, unrestricted or unimpeded expansion shape.

Figure 10:
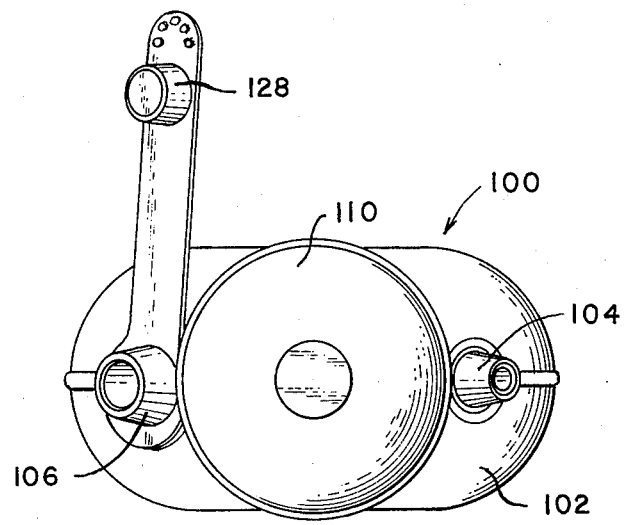
FIG. 10 is a top view of the wound evacuator of FIG. 9.
Figure 9:
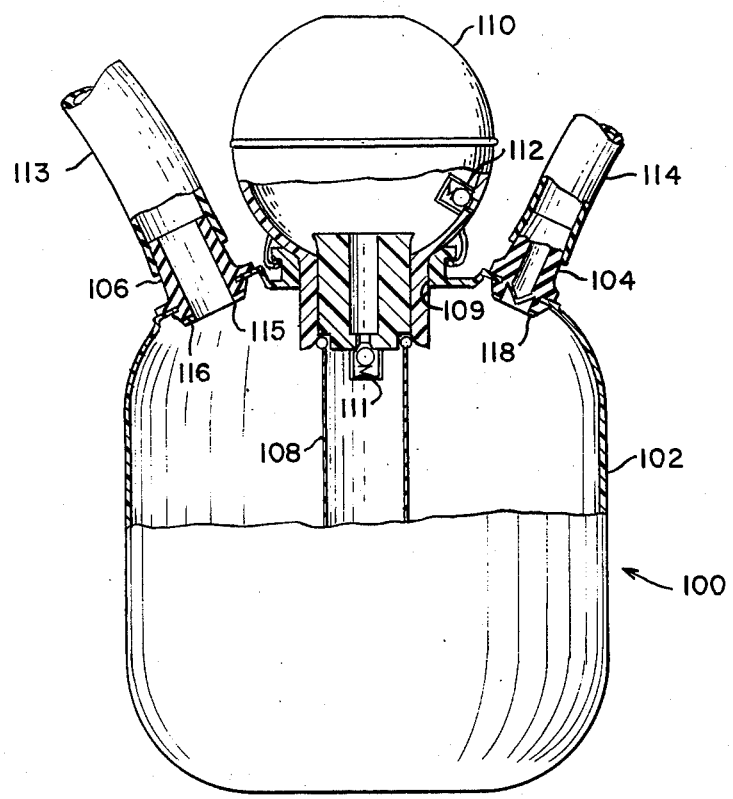
FIG. 9 is a partial sectional view of a wound evacuator formed in accordance with another embodiment of this invention.

In accordance with the invention, a wound evacuator having inlet and outlet ports designed to control the sequence of sealing is illustrated in FIGS. 9 and 10. As here embodied, a self-contained wound evacuator 100 adapted for use with an external vacuum source (not shown) is formed with a container 102 having an inlet port 104 and an outlet port 106 extending through and communicating with the interior of the container 102. The inlet and outlet ports 104, 106, respectively, may be formed as an integral part of the container 102 (as is illustrated in FIG. 2) or may be formed as a separate member mounted in an opening formed in the container 102 as is illustrated in FIG. 9.

An air-inflatable member, for example, a resilient bladder 108 mounted on a means for inflating the bladder such as a hand-operated bulbous resilient member 110, is mounted in an opening 109 through the container 102. The bulb 110 is provided with a suitable opening to receive external air and appropriate valve means are provided between the bulb 110 and the bladder 108 to permit free flow of air from the bulb 110 to the bladder 108 when the bulb is squeezed to force air into the bladder and to control the flow rate of air from the bladder 108 to the bulb 110 upon release of the bulb. Any suitable imperfect check valve can be used for this purpose. For example, a ball check valve 111 having either a roughened surface or a roughened valve seat would permit a limited flow rate from the bladder 108 to the bulb 110. Another means is to provide a small bleed passageway through or on the side of the ball valve or seat. A similar imperfect check valve 112 can be used with the bulb 110 to permit free flow of air from the atmosphere into the bulb and limited flow rate of air from the bulb to the atmosphere. This will enable the bulb 110 to fill quickly and will force most of the air to flow into the bladder.

As explained above with respect to the embodiments illustrated in FIGS. 1–8, the bladder 108 is expanded by squeezing the bulb 110 and forcing air into the bladder, the air between the bladder and the container interior walls being forced out through an outlet port. When the bladder 108 is fully expanded, the outlet port 106 is closed by plug 128 and air is permitted to leave the bladder through its check valve 111 at a controlled rate causing a reduced pressure to exist at the inlet port 104 providing the necessary suction to remove fluid from the patient. When the container 102 is full, it must be emptied, the bladder reinflated, and the process repeated.

When it is desired to have continous fluid evacuation from a wound, the outlet port 106 of the fluid evacuator 100 is attached for fluid flow communication with an external vacuum source by means of flexible tubing 113 mounted on the outlet port 106. The inlet port 104, of course, is adapted to receive conventional wound tubing 114.

To utilize the wound evacuator 100 as a continuous evacuator, such as during an operation or closing of a wound, the distal end of the wound tubing 114 is inserted in the patient and the interior of the wound evacuator container 102 is then subjected to the negative pressure source, such as a vacuum pump. Fluid from the wound freely flows into the container 102 through the inlet port 104 and it passes through the outlet 106 to the vacuum source. This continuous fluid evacuation continues as long as required without the need for intermittant emptying of the container 102 and reinflation of the bladder 108. If the pressure within the container 102 is reduced sufficiently below atmospheric presure, the bladder 108 will inflate as a result of air entering the bladder from the atmosphere through the bulb 110 and bladder 108 passageways.

Figure 11:
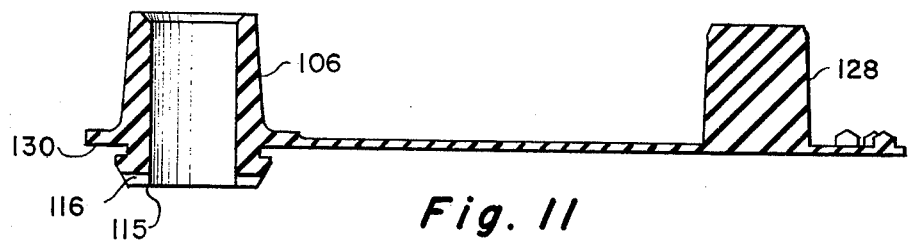
FIG. 11 is a sectional view of an outlet port used in the wound evacuator of FIG. 9.
Figure 12:
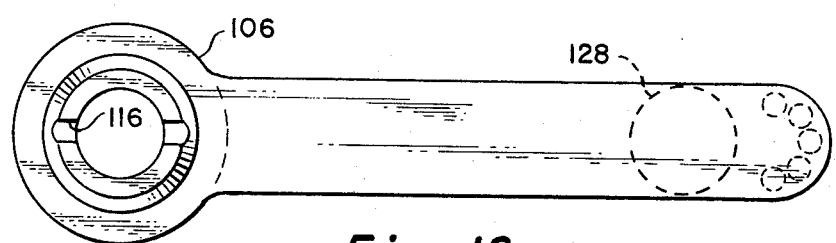
FIG. 12 is a bottom view of the outlet port of FIG. 11.
Figure 13:
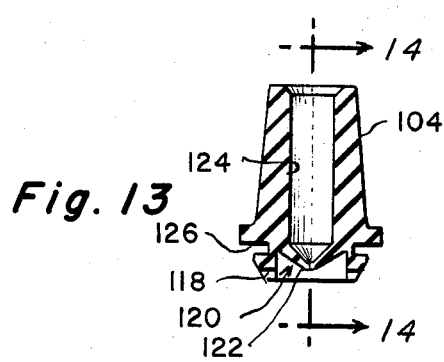
FIG. 13 is a sectional view of an inlet port used in the wound evacuator of FIG. 9.
Figure 14:
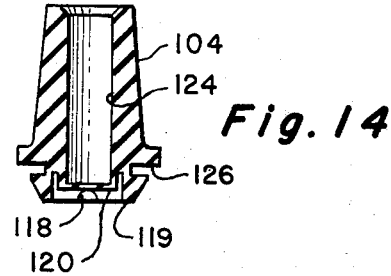
FIG. 14 is a sectional view taken along line 14—14 of FIG. 13.
Figure 15:
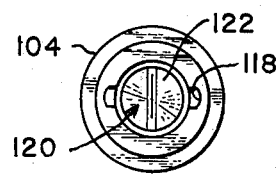
FIG. 15 is a bottom view of the inlet port of FIG. 13.

It is important to prevent the bladder 108 from sealing off the inlet port in order to ensure continued fluid-flow communication between the inlet port 104 and the vacuum source through the outlet port 106 and the container 102. Accordingly, suitable means must be provided to ensure that the inlet port 104 is not obturated by the bladder 108. One means for preventing sealing of the inlet port 104 is the formation of a discontinuous surface at the mouth 119 of the inlet 104. As here embodied, recesses or notches 118 are formed at the mouth 119 of the inlet port 104 as is best illustrated in FIGS. 13, 14, 15. Similarly, in order to preclude inadvertent sealing of the outlet port 106 if so desired, recesses or notches 116 are provided at the mouth 115 of the outlet port 106 as is best illustrated in FIGS. 11 and 12. These notches 116, 118 ensure continued fluid flow communication from the inlet port 104 to the outlet port 106.

For certain applications, it may be desired to seal the outlet port prior to the inlet port, or visa-versa. In that case, the port which is desired to be sealed first would not be provided with notches thereby permitting the bladder to obturate the appropriate port. For example, if as described above, the container 102 is not appropriately shaped to conform to the unimpeded inflated shape of the bladder 108, an effective configuration can be achieved by causing the bladder 108 to obturate the outlet port 106 immediately prior to the moment when the bladder is about to be deformed from its unimpeded expansion shape by virtue of contact with the container walls. Therefore, the mouth of the outlet port 106 would not be provided with the notches 116 allowing the outlet port to be obturated or sealed by the bladder 108.

Another example for sealing the outlet port prior to the inlet port would be to permit the bladder to serve as a regulator or limiting valve assuring a safe limit of vacuum being applied to the inlet port 104. As the vacuum within the container 102 increases, the bladder 108 will inflate and, if for some reason, such as blockage of the inlet tube 114, insufficient flow of fluid enters the container 102 thereby permitting the vacuum within the container to continue to increase, the bladder will ultimately expand to fill the container and seal the outlet valve thereby preventing further evacuation of the container 102. The vacuum value at which the bladder would seal the outlet port 106 would be approximately the same as that which the bladder itself would create in normal use if it was inflated by use of the bulb 110 and, therefore, would be a safe vacuum level. If outlet port, 106, is provided with means to prevent sealing of this port by the bladder, then it is preferred that a pressure regulator (not shown) be provided in the vacuum source line to assure a safe vacuum limit being applied to the inlet port 104.

As is illustrated in FIGS. 13–15, the inlet port 104 may be formed as a separate member such as by molding. The inlet port 104 also includes a check valve 120 integrally formed as a part thereof. The check valve is formed by molding a V-shaped wall or disc 122 across the inlet passageway 124 through the inlet port 104 and subsequently slitting the V-shaped wall at its apex thereby forming two flaps or lips. In this manner, when the pressure differential across the check valve 120 is such that a lower pressure is in the container 102 as contrasted with the inlet port passageway 124, such as when fluid is being removed from the patient, the slit opens and fluid is permitted to pass therethrough. However, if pressure within the container 102 exceeds the pressure within the inlet port passageway 124, pressure will tend to force the lips of the V-shaped wall together thereby closing the slit and preventing fluid flow from the container 102 into the inlet passageway 124 and ultimately to the patient. The check valve 120 is recessed with respect to the mouth 119 of the inlet port 104 to ensure that the bladder 108 does not interfere with proper operation of the check valve. An annular groove 126 also is formed near the mouth 119 of the inlet port 104 to permit the inlet port 104 to be snap-fitted into an aperture through the walls of the container 102.

The outlet port 106 also can be molded as a separate member (FIGS. 11 and 12) and a closure plug 128 can be formed as an integral part thereof. An annular groove 130 is formed adjacent the mouth 115 for mounting the outlet port on the container 102.

The inlet port 104 and the outlet port 106 may be formed of any non-toxic, non-pyrogenic material suitable for molding. One example of a suitable material is natural rubber. Natural rubber also has the proper flexibility and resiliency to make it ideal for proper operation of the check valve.

Figure 16:
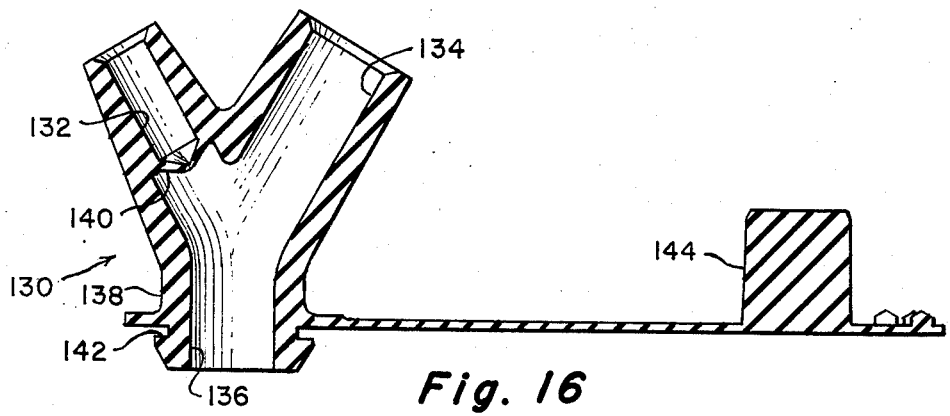
FIG. 16 is a sectional view of a combined inlet-outlet port.

In place of using separate inlet and outlet ports and means such as grooves to control the sequence of closure of the ports by the inflatable member, a combined inlet and outlet port with separate passageways could be employed. Referring to FIG. 16 there is illustrated a Y-shaped combined inlet-outlet port 130 having an inlet passageway 132, an outlet passageway 134 and a common passageway 136 through the neck 138 through which the inlet and outlet passageways communicate with the interior of the container 102. A check valve 140 is formed or otherwise mounted across the inlet passageway 132 and an annular groove 142 is formed on the outside of the neck 138 to enable the port 130 to be mounted on the container. An outlet port closure plug 144 is formed as part of the port 130 to facilitate closing the outlet passageway 134 when the wound evacuator is to be used as a self-contained unit.

Because only a single mouth or port entrance is used for the combined inlet-outlet port 130, there is no danger that one of the passageways 132, 134 could be obturated before the other by the inflatable bladder 108.

Fluid may be evacuated continuously from a wound by connecting the inlet passageway 132 to a wound by wound tubing. After the wound site is closed, the wound evacuator is disconnected from the vacuum source and used as a self-contained evacuator which fluid being collected in the container through use of the inflatable bladder.

SUMMARY

It can be seen that the fluid evacuator of this invention is completely self-contained, portable and totally reliable, as well as being adapted for use with a vacuum source as a continuous evacuator. It is also easy and inexpensive to manufacture and, therefore, disposable. Of considerable significance are the safety features which prevent the fluid evacuator from being accidentally pressurized in a manner which will inject air or previously removed fluids back to the patient. Furthermore, the negative pressure formed at the inlet port which causes the forced removal of fluid from the patient is substantially constant thereby, (a) avoiding potential injury to the patient which could occur if the negative pressure is too high and (b) ensuring efficient operation of the evacuator throughout the entire operational range of the wound evacuator.

What is claimed is:

1. A self-contained fluid evacuator comprising a substantially rigid container having an inlet passageway and an outlet passageway communicating with the interior thereof, an inflatable member within said container, inflating means for inflating said inflatable member, means for deflating said inflatable member, said inlet passageway being adapted to receive a conduit, said outlet passageway being adapted to be connected in fluid flow communication with a negative pressure source, and means for ensuring that a predetermined one of said inlet and outlet passageways does not become obturated by said inflatable member before the other of said inlet and outlet passageways.

2. A self-contained fluid evacuator as defined in claim 1 including flow control means for enabling fluid to enter said inflatable member at a higher rate than the fluid can leave said inflatable member.

3. A self-contained fluid evacuator as defined in claim 2 wherein said flow control means is a check valve having means for permitting air to escape at a predetermined rate through said check valve when said check valve is seated.

4. A self-contained fluid evacuator as defined in claim 2 wherein said container includes first and second spaced apart opposed side walls, and third and fourth side walls joined to the opposite ends of said first and second side walls, said third and fourth side walls being spaced apart a distance greater than the spacing between said first and second walls, said third and fourth side walls having a configuration which substantially conforms to the shape of the natural unimpeded shape of the adjacent portion of said inflatable member during inflation of said inflatable member effecting substantially constant negative pressure at said inlet passageway during deflation of said inflatable member and including means for closing said outlet passageway.

5. A self-contained fluid evacuator as defined in claim 4 wherein said inflatable member is a substantially cylindrical bladder and wherein said first and second side walls are substantially flat thereby giving said container a low profile.

6. A self-contained fluid evacuator as defined in claim 1 wherein said ensuring means includes means for communicating both said inlet and outlet passageways with the portion of the interior of said container outside the inflatable member through a single port through said container.

7. A self-contained fluid evacuator as defined in claim 6 including means for closing said outlet passageway and flow control means for enabling fluid to enter said inflatable member at a higher rate than the fluid can leave said inflatable member.

8. A self-contained fluid evacuator comprising a substantially rigid container, an inflatable member within said container, means for inflating said inflatable member, means for deflating said inflatable member, an inlet passageway extending through said container and having a mouth projecting inwardly from the interior surface of said container, an outlet passageway extending through said container and having a mouth projecting inwardly from the interior surface of said container, at least one of the inlet passageway mouth and outlet passageway mouth having a recessed portion to ensure that the passageway mouth having the recessed portion does not become obturated by said inflatable member before the other passageway mouth, said outlet passageway being adapted to be placed in fluid flow communication with a negative pressure source.

9. A self-contained fluid evacuator as defined in claim 8 including means for closing said outlet passageway and flow control means for enabling fluid to enter said inflatable member at a higher rate than the fluid can leave said inflatable member.

10. A self-contained fluid evacuator as defined in claim 8 wherein said recessed portion is a notch provided in the mouth of said outlet passageway.

11. A self-contained fluid evacuator as defined in claim 8 wherein said recessed portion is a notch provided in the mouth of said inlet passageway.

12. A self-contained fluid evacuator as defined in claim 8 wherein said recessed portion is a notch provided in the mouth of each of said inlet and outlet passageways.

13. A self-contained fluid evacuator comprising:
a. a substantially rigid, closed container including a bottom wall, first and second spaced apart opposed side walls, third and fourth side walls joined to the opposite ends of said first and second side walls, said third and fourth side walls being spaced apart further than said first and second side walls;
b. a resilient inflatable member within said container;
c. means for inflating said inflatable member mounted on said container and communicating with said inflatable member;
d. an inlet port communicating with the interior of said container and adapted to receive a conduit;
e. an outlet port communicating with the interior of said container and adapted to receive a conduit, the wall of said inlet port having a recessed portion to ensure that said inlet port is not obturated by said inflatable member before said outlet port;
f. means to close said outlet port;
g. said third and fourth side walls having an effective configuration which conforms to the shape of the natural unimpeded shape of the adjacent portion of said inflatable member during inflation of said inflatable member effecting substantially constant negative pressure at said first port during deflation of said inflatable member.

14. A self-contained fluid evacuator as defined in claim 13 wherein said inflatable member occludes said outlet port when said inflatable member and said third and fourth side walls obtain a predetermined relationship thereby terminating the expulsion of air from said container, said predetermined relationship being that further inflation of said inflatable member without occlusion of said outlet port would produce deformation of said inflatable member into a shape which it would not take if said third and fourth walls were non-existent.

15. A self-contained fluid evacuator comprising a substantially rigid container, an inflatable member within said container, first means for inflating said inflatable member, second means for deflating said inflatable member, said container having first and second apertures therethrough, an inlet port having a passageway therethrough mounted in said first aperture, an outlet port having a passageway therethrough mounted in said second aperture, at least one of said ports being formed with third means for ensuring that such inflatable member does not obturate the port with said third means before said inflatable member obturates the other of said ports, said outlet port being adapted to be connected in fluid flow communcation with a negative pressure source, and fourth means for closing said outlet port.

16. A self-contained fluid evacuator as defined in claim 15 where said inlet port includes mounting means for securing said port to said container and a check valve across the inlet passageway molded as an integral part of said inlet port.

17. A self-contained fluid evacuator as defined in claim 16 wherein said third means includes a mouth portion for said inlet port spaced inwardly toward the interior of said container from the interior surface of said container, said mouth portion having a notch formed therein to prevent said inflatable member from obturating said inlet port.

18. A self-contained fluid evacuator as defined in claim 16 including flow control means for enabling fluid to enter said inflatable member at a higher rate than the fluid can leave said inflatable member.

19. A self-contained fluid evacuator as defined in claim 18 wherein said flow control means is a check valve having means for permitting air to escape at a predetermined rate through said check valve when said check valve is seated.

20. A self-contained fluid evacuator as defined in claim 19 wherein said container includes first and second spaced apart opposed side walls, and third and fourth side walls joined to the opposite ends of said first and second side walls, said third and fourth side walls being spaced apart a distance greater than the spacing between said first and second walls, said third and fourth side walls having a configuration which substantially conforms to the shape of the natural unimpeded shape of the adjacent portion of said inflatable member during inflation of said inflatable member effecting substantially constant negative pressure at said inlet passageway during deflation of said inflatable member and including means for closing said outlet passageway.

21. A self-contained fluid evacuator as defined in claim 15 where said inlet port includes a check valve formed as an integral part of said inlet port across the inlet passageway and spaced from the end of said inlet port adjacent to said container in order to prevent said inflatable member from interfering with operation of said check valve.

22. A self-contained fluid evacuator as defined in claim 21 where said check valve comprises a disc having a V-shaped cross-section and a slit through the apex of said disc, the base of said disc joining the walls defining the inlet passageway at a position further from said container than the apex of said disc.

23. A self-contained fluid evacuator as defined in claim 22 wherein said inlet port is molded of natural rubber.

* * * * *